(12) United States Patent
Salasidis

(10) Patent No.: US 11,994,270 B2
(45) Date of Patent: May 28, 2024

(54) METHOD AND APPARATUS FOR AUTOMATICALLY FOCUSING OVERHEAD LIGHT

(71) Applicant: Kayla Salasidis, Saint-Laurent (CA)

(72) Inventor: Kayla Salasidis, Saint-Laurent (CA)

(73) Assignee: Kayla Salasidis, Saint-Laurent (CA)

( * ) Notice: Subject to any disclaimer, the term of this patent is extended or adjusted under 35 U.S.C. 154(b) by 0 days.

(21) Appl. No.: 18/125,813

(22) Filed: Mar. 24, 2023

(65) Prior Publication Data

US 2023/0313976 A1 Oct. 5, 2023

Related U.S. Application Data

(60) Provisional application No. 63/325,436, filed on Mar. 30, 2022.

(51) Int. Cl.
*F21V 14/02* (2006.01)
*A61B 90/30* (2016.01)
*F21V 23/04* (2006.01)
*H05B 47/115* (2020.01)
*F21Y 115/10* (2016.01)

(52) U.S. Cl.
CPC ............ *F21V 14/02* (2013.01); *A61B 90/30* (2016.02); *F21V 23/0471* (2013.01); *H05B 47/115* (2020.01); *F21Y 2115/10* (2016.08)

(58) Field of Classification Search
CPC ....... F21V 14/02; F21V 23/0471; A61B 90/30
See application file for complete search history.

(56) References Cited

U.S. PATENT DOCUMENTS

| 4,884,008 A | 11/1989 | Bossler et al. |
| 11,153,953 B2 * | 10/2021 | Alexanderson ..... F21V 23/0471 |
| 2013/0113909 A1 * | 5/2013 | DeLand ................. A61B 50/28 |
| | | 348/77 |
| 2017/0254522 A1 * | 9/2017 | Liang .................. F21V 23/0435 |

FOREIGN PATENT DOCUMENTS

WO WO-2021239873 A1 * 12/2021 ............. A61B 90/30

* cited by examiner

*Primary Examiner* — Karabi Guharay
(74) *Attorney, Agent, or Firm* — PERRY + CURRIER INC.

(57) ABSTRACT

An overhead lighting system is set forth comprising a master module having a sensor for measuring distance to an area of interest, and at least one peripheral module pivotally connected to the master module, the at least one peripheral module having at least one lamp and a mechanism for pivoting the at least one peripheral module to an angle relative to the master module based on the distance to the area of interest, for focusing the at least one lamp on the area of interest.

19 Claims, 7 Drawing Sheets

METHOD AND APPARATUS FOR AUTOMATICALLY FOCUSING OVERHEAD LIGHT

BACKGROUND OF THE INVENTION

1. Field of the Invention

The present invention is directed to adjustable overhead lamps, and more particularly to an automatically focusing overhead lighting system useful in an operating room.

2. Description of the Related Art

Proper operating room (OR) lighting is critical for comfort of the surgical team and patient safety and should be designed to enable the medical team to focus exclusively on the surgical procedure. Typical OR lamps include a plurality of lamps (e.g. LED lights) arranged such that light beams overlap in a specific operating region to increase light intensity in that region and to eliminate shadows. Handles may be provided on the OR lamps, for example at the edges thereof, to adjust the spacing of the lights with respect to a region of interest. Electric motors can also be provided to adjust the positions of the lamps so that the light beams overlap.

Generally, prior art OR lamps require manual positioning and focusing by the surgical team. As a result, many surgeons spend significant amounts of time directing and redirecting light to areas of interest during a surgical procedure, which can lead to distraction and frustration. In fact, a recent study has shown that during the course of a surgical procedure, hospital OR staff must reposition the lights on average every 7.5 minutes. Thus, over the course of a four hour operation, the lights have to be manipulated thirty-two times on average. This is not only distracting for the OR staff during the procedure but is also time consuming, which can lead to an increase in costs to the hospital. Adequate surgical lighting is critical for patient safety and OR staff comfort and should be designed to enable the medical team to focus exclusively on the surgical procedure.

Three aspects of surgical lights are important for effective illumination: a light source should firstly center on the surgical field, secondly illuminate with high intensity, and thirdly penetrate into a deep surgical cavity. These aspects are important in reducing eye fatigue and strain.

One prior art OR lamp is described in U.S. Pat. No. 4,884,008 (Bossier et al.), which provides for automatic adjustment of the light field of an operating room light in accordance with manual positioning of a surgical light. An electrical servo control loop positions the respective lamps and/or deflection mirrors of circularly placed light sources in a housing to illuminate a given field in a given plane.

SUMMARY OF THE INVENTION

This specification describes an embodiment of an overhead lighting system that facilitates positioning and automatically focuses light on a region such as a surgical site. The described embodiment utilizes a distance sensor that measures the distance to the surgical site and focuses its light once moved. Features are also set forth to improve the quality of illumination and thereby address the needs of surgeons, such as color temperature, focus size and brightness, for improving visualization of the surgical site. It is an object of this specification to describe a system that will save time and cost of surgery, improve staff comfort and reduce surgical error.

It is an aspect of the present invention to provide an overhead lighting system comprising a master module having a sensor for measuring distance to an area of interest, such as a surgical site, and at least one peripheral module pivotally connected to the master module. The peripheral module has at least one lamp and a mechanism for pivoting the peripheral module, when the master module is moved, to an angle relative to the master module based on the distance to the area of interest, thereby focusing at least one lamp on the area of interest.

These together with other aspects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENTS

Figure 1:
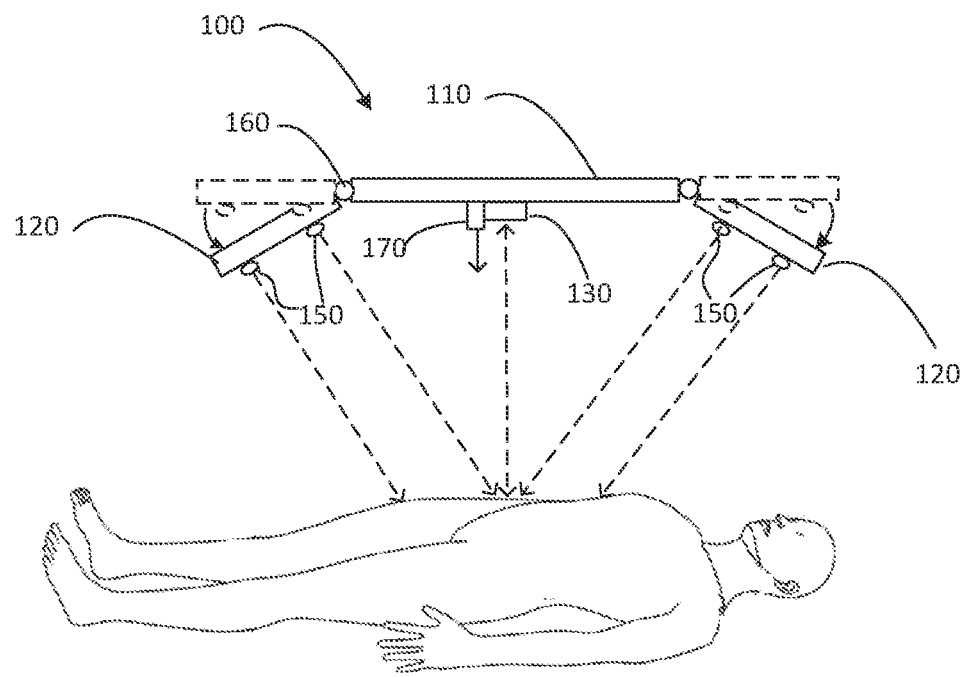
FIG. 1 is a schematic diagram of an overhead lighting system having a master module and one or more peripheral modules, according to an embodiment.

FIG. 1 shows an overhead lighting system 100 according to an embodiment. System 100 is of modular design comprising a master module 110, and at least one peripheral module 120, sometimes referred to as a petal board, pivotally connected to the master module 110. Master module 110 includes a sensor 130 (e.g. LIDAR-Lite v3HP available from Garmin) for measuring distance to an area of interest (with a very small spot size). The master module, also includes a laser crosshair (170), positioned colinear with the LIDAR sensor, as well as immobile LED lighting for coaxial illumination. Each peripheral module 120 includes at least one lamp 150 and a pivot mechanism 160. Pivot mechanism 160 is used to automatically pivot the peripheral module 120 to an angle relative to the master module based on the distance to the area of interest, for focusing the lamp 150 on the area of interest.

Figure 2:
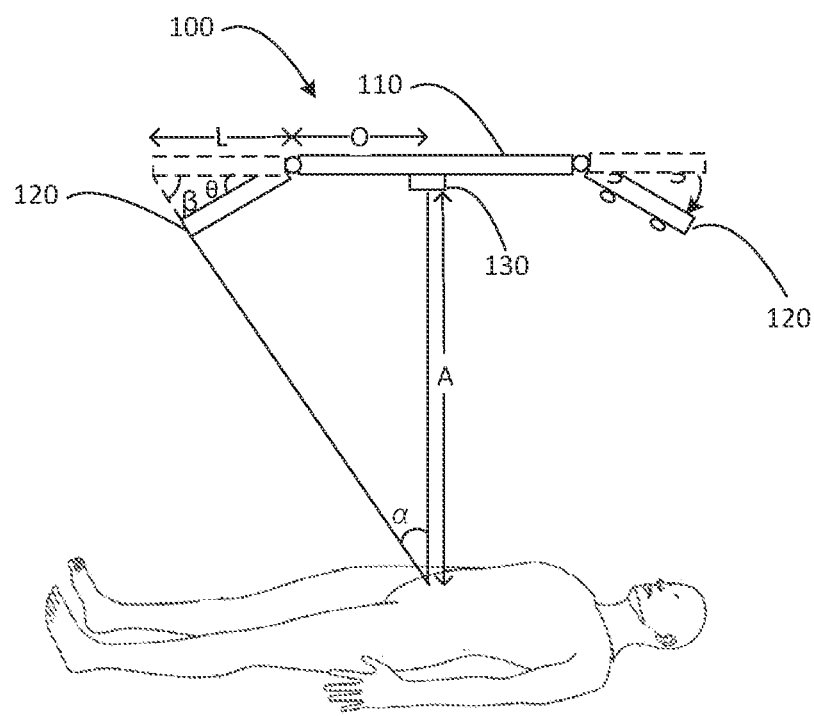
FIG. 2 shows general trigonometric calculations of pivot angle of the one or more peripheral modules to the central master module of FIG. 1, according to an embodiment.

Master module 110 calculates the pivot angle of the peripheral module 120 using trigonometry based on the average distance A read by the sensor 130, to the area of interest, distance O of the sensor 130 to the edge of the master module 110, and distance L from the pivot point of the pivot mechanism 160 to the edge of peripheral module 120, as shown in FIG. 2. The distance A is perpendicular to the distance O, forming a right-angle triangle, with O being opposite of an angle $\alpha=\tan^{-1}(O+L/A)$. Since $\alpha=180-(90+\beta)$, then $\alpha=90-\beta$ and $\theta=90-\beta$, so $\alpha=\theta$, which is the angle necessary for the peripheral module 120 to focus lamp 150 on the area of interest.

In some embodiments, the master module 110, as well as the pivot mechanism 160 can be designed as a single control unit, as opposed to a master hub, spoke design, and individual pivots can be controlled by a single motor, all of which are design variations that are independent of the function of the overhead lighting system 100.

In an embodiment, modules 110 and 120 can communicate using Inter-Integrated Circuit (I2C) protocol according to a master-slave configuration wherein the master module 110 controls the one or more peripheral modules 120. I2C is a synchronous, multi-controller/multi-target (controller/target), packet switched, single-ended, serial communication bus for intra-board communication. The I2C protocol specifies transmission of data and clock signals between the modules over a serial bus.

Figure 3:
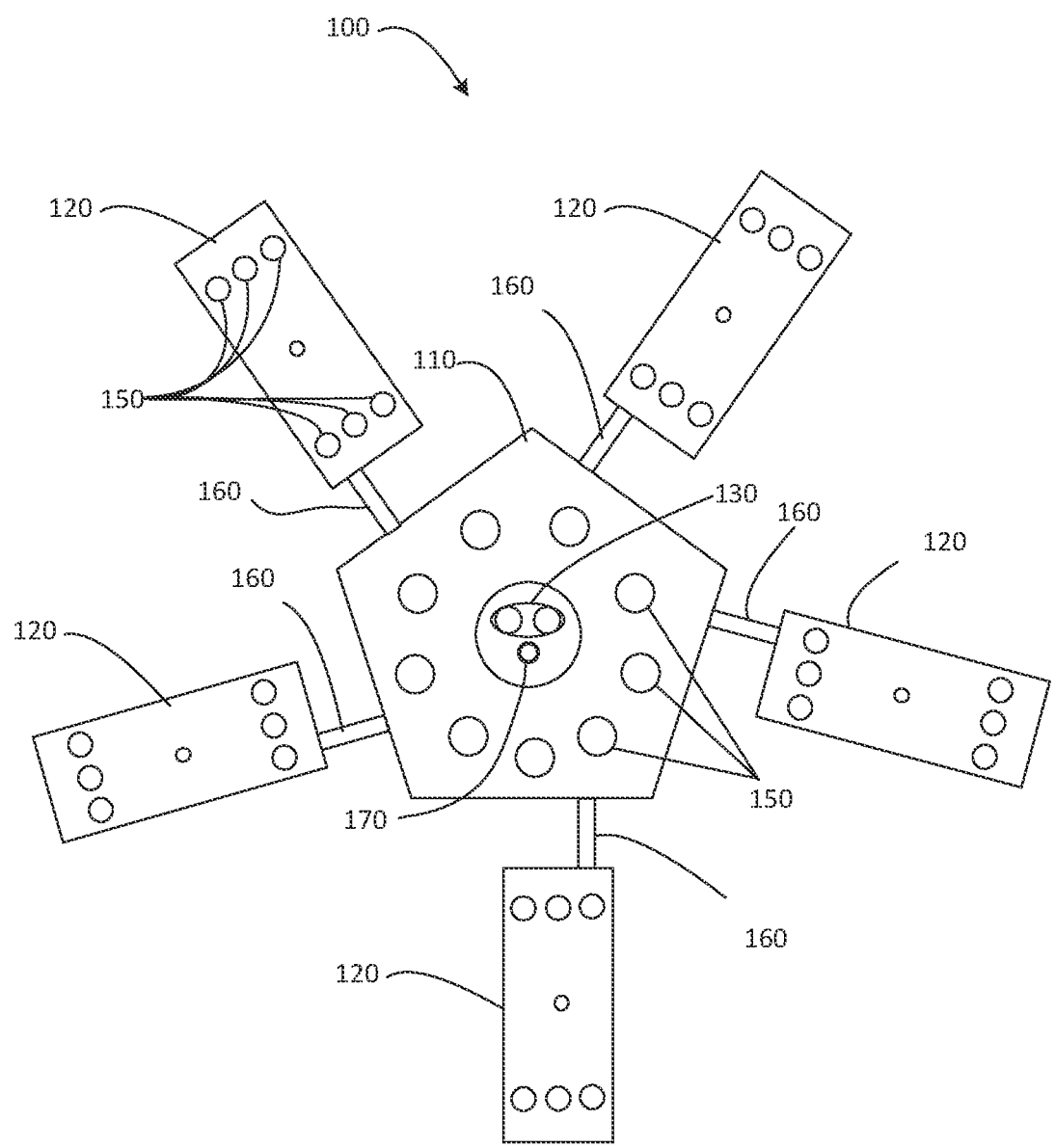
FIG. 3 shows an arrangement of five peripheral modules pivotally connected to a central master module, according to an embodiment.

Turning to FIG. 3, an embodiment of overhead lighting system 100 is shown comprising five peripheral modules 120 connected to master module 110 via pivot mechanisms 160, wherein master module 110 includes additional lamps 150.

Figure 4:
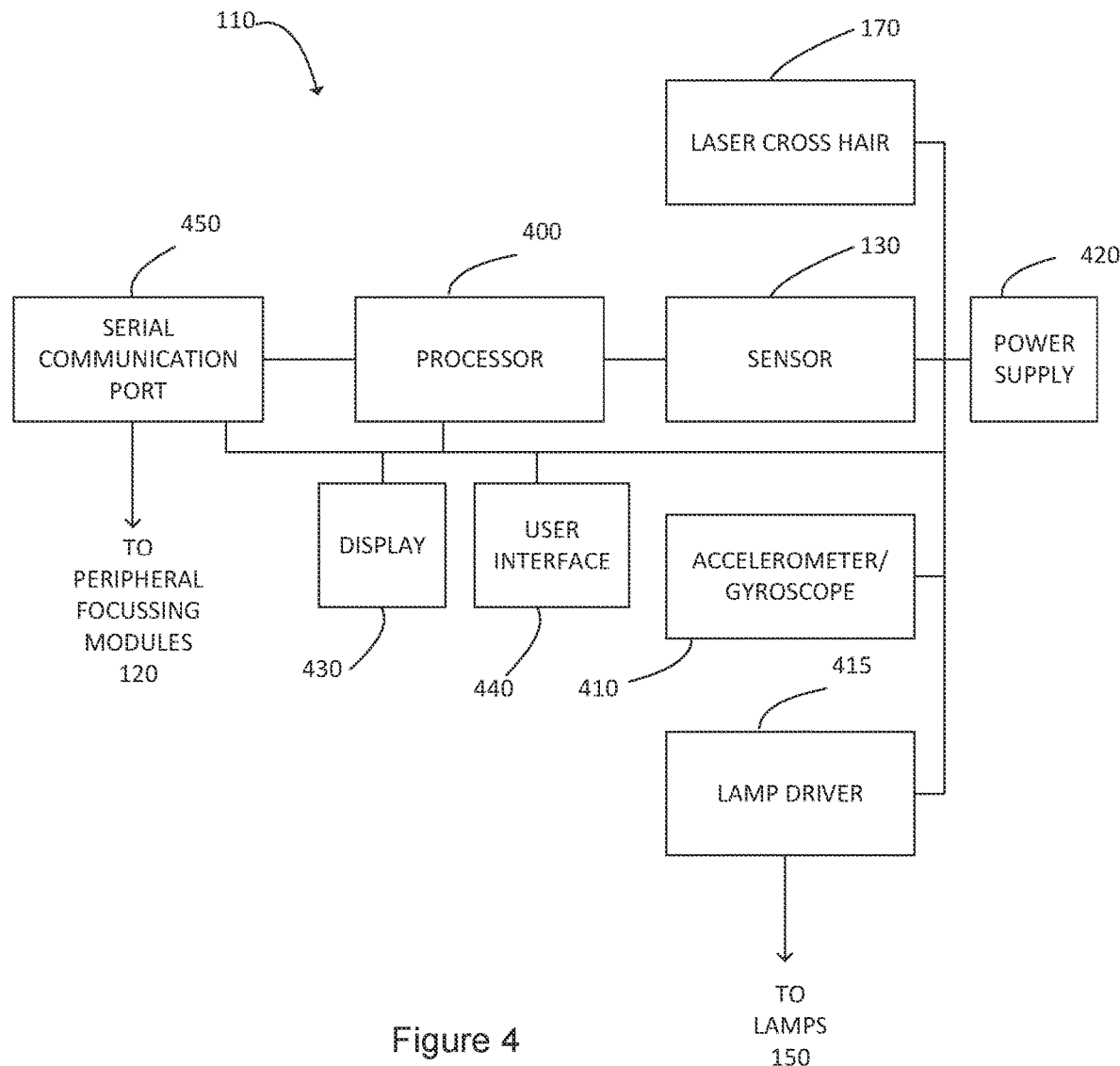
FIG. 4 is a block diagram showing electronic components of a central master module, according to an embodiment.

As shown in FIG. 4, internal components of the master module 110 can include a processor 400 connected to distance sensor 130, laser crosshair 170, an accelerometer/gyroscope 410 (e.g. an LSM6DSO available from ST Micro) to measure acceleration and rotation in three dimensions (XYZ), lamp driver 415 for driving lamps 150, a power supply 420 (e.g. (12V/25 Amps available from Digikey), a display 430 (e.g. LCD display), user interface 440 (e.g. three button interface, and a serial communication port 450 for connection to the peripheral modules 120 via the I2C protocol. Note that multiple peripheral modules 120 can be connected to the master module 110 via a daisy chain, hub and spoke or other configuration subject to I2C cable length between the modules, which can be extended by adding buffers, and/or active terminators in the I2C to allow longer total cable lengths.

Preferably, processor 400 includes or is connected to an on board EEPROM (Electrically erasable programmable read only memory) that stores lamp operating parameters, so that after the system 100 has been turned off and is thereafter turned on again, the last used parameters (focus, color, etc.) can be restored.

Figure 5:
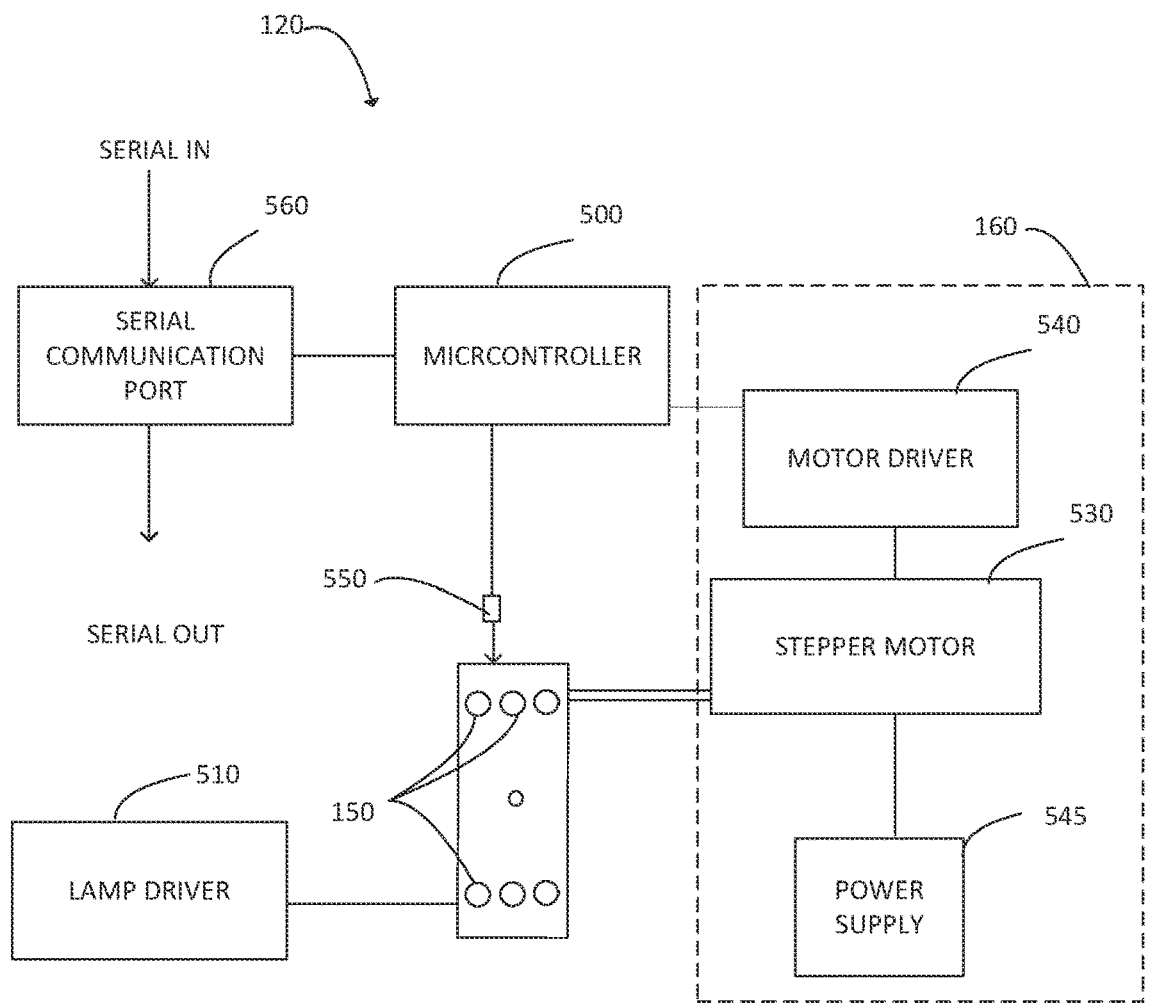
FIG. 5 is a block diagram showing electronic components of a peripheral modules, according to an embodiment.

As shown in FIG. 5, each peripheral module 120 includes a microcontroller 500 (e.g. Nano V3 incorporating software application programming interfaces (APIs), including FreeRTOS, available from Arduino), for controlling operation of module components in conjunction with master module 110 over the I2C serial communication bus.

A lamp driver 510 (e.g. Picobuck LED driver available from Sparkfun) provides signals for controlling LEDs 150. The control can vary the kelvin color temperature and brightness of the LEDs 150 (e.g. Cree XPE LEDs (3000, 4500, 6200 kelvin available from Digikey, attached to reflector lenses to create bright narrow beams of light. Two rows of LEDs allows for a smaller spot size when the outer row is bypassed (rows connected in series, wherein bypassing a row will turn it off without affecting brightness of the inner row). The three separate LED colors, 3000, 4500 and 6200 degrees Kelvin, have their brightness adjusted individually by the lamp driver 510 by means of pulse width modulation (PWM) signals, as discussed in greater detail below with reference to FIG. 9.

A stepper motor 530 (e.g. dual shaft stepper motor 17/STP-MTR-17048D available from NEMA) is provided under control of a motor driver 540 (e.g. ROB-12859 loaded with a preexisting Arduino library available from Sparkfun). Power is supplied to the stepper motor 530 from a power supply 545 (e.g. a 12 Volt/25 Amp power supply of four Amps at three Volts each). Collectively, stepper motor 510, motor driver 520 and power supply 545 comprise the pivot mechanism 160 for positioning the focus of lamps 150 by angling the peripheral module 120 relative to the master module 110, as discussed above. In order to set the zero position of the stepper motor 530, a proximity sensor/absolute encoder 550 is provided (e.g. an NPN proximity sensor for generating a control signal when a surface of peripheral module 120 is moved by stepper motor 530 into range of the proximity sensor/absolute encoder 550 as it nears a horizontal orientation. A dual shaft design is used in case a shaft break is used during periods of no motion, to decrease overall current consumption.

A serial communication port 560 is provided for communication between peripheral modules 120 and master module 110 over the I2C serial communication bus. For example, in an embodiment, each row of lamps 150 (e.g. LEDs) can be connected in series with pins on the communication port 560 can be provided to shut down a row of LED lamps by shorting the LED lamps using MOSFET switches to select between all rows of LED lamps, or only the central rows of lamps in order to regulate spot size, while other pins can be used to control color (3000, 4500, 6200 K).

Figure 6:
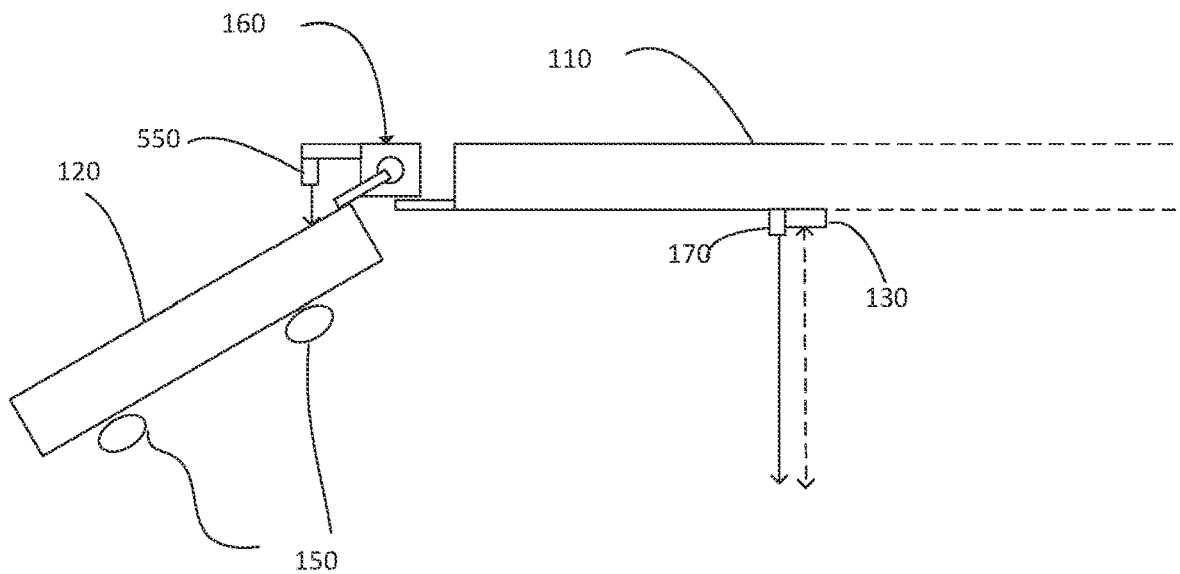
FIG. 6 is a detail view of the pivot mechanism connecting the master module to a peripheral module, in accordance with an embodiment.
Figure 7:
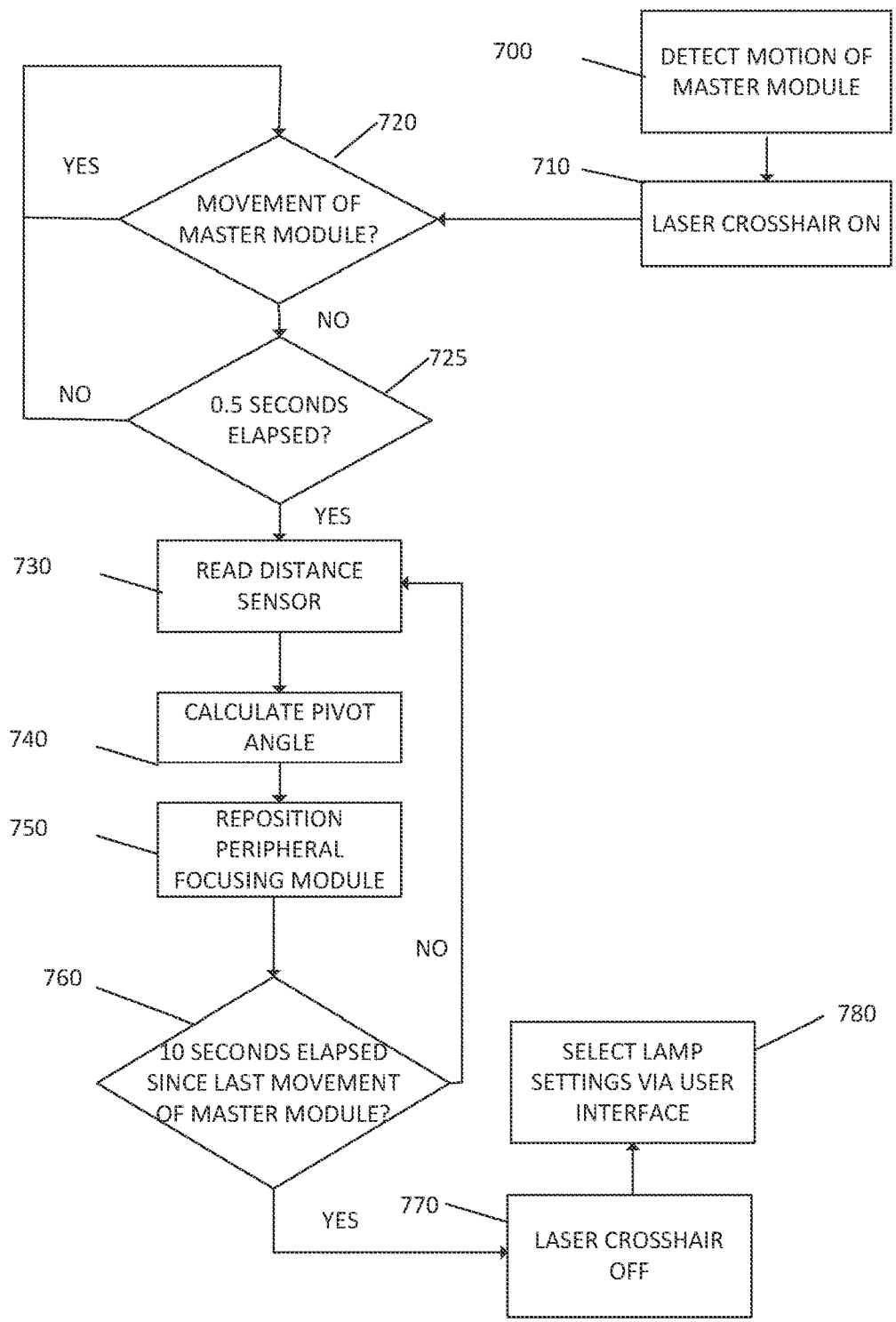
FIG. 7 is a flowchart showing operation of an overhead lighting system, in accordance with an embodiment.

Details of operation may be understood by reference to FIG. 6, which is a partial detail view of peripheral modules 120 and master module 110, in conjunction with the flowchart in FIG. 7. At 700, when accelerometer/gyroscope 410 detects motion of the master module 110 (e.g. a surgeon moving the module into position over a patient), laser crosshair 170 is turned on at 710, to enable the surgeon to pinpoint the desired lighting position for the overhead lighting system 100. Provided the master module 110 has stopped moving for a short time period (e.g. approximately 0.5 seconds)—a NO at 720 and YES at 725), distance sensor 130 is read a number of times (over a few milliseconds) and the data is averaged at 730. The pivot angle is then calculated at 740 within master module 110, as discussed above, and stepper motor 530 then moves the peripheral module 120 to a new focus position, at 750, based on the averaged distance measured by distance sensor 130. At 760, after accelerometer/gyroscope 410 detects no further motion of the master module 110 for a longer time period (e.g. approximately 10 seconds), the laser crosshair 170 turns off at 770, to avoid surgical distractions (the shaft break can be applied if available and required). Thereafter, at 780, the surgeon can interact with user interface 440 and display 430 to scroll through and select menu items, including color, brightness, spot size, focus offset, and manual reset.

Figure 8:
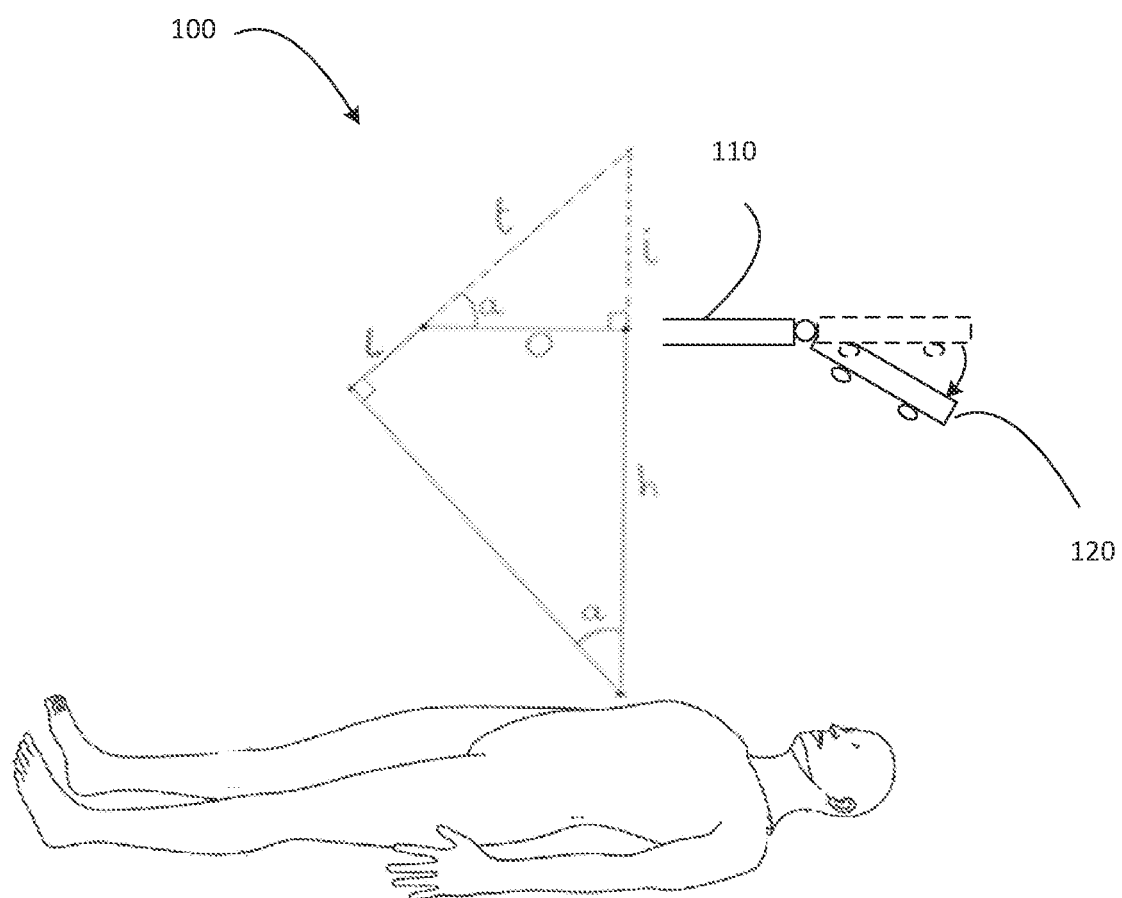
FIG. 8 shows trigonometric calculations of pivot angle, in accordance with a further embodiment.

The general trigonometric calculation of the pivot angle set forth above with reference to FIG. 2, includes an inherent error that increases with shorter focus distances or a greater length L. However, a modification of the general calculation allows for determination of the focus height h, from any given angle, as shown in FIG. 8. Specifically:

$$\sin(\alpha) = 1 + t/h + i$$

$$\tan(\alpha) = i/o$$

$$j = \tan(\alpha) * o$$

$$\sin(\alpha) = 1 + t/[h + (\tan(\alpha)*o)]$$

$$\cos(\alpha) = o/t$$

$$t = o/\cos(\alpha)$$

$$\sin(\alpha) = [1 + (o/\cos(\alpha))]/[h + (\tan(\alpha)*o)]$$

$$\sin(\alpha) * [h + (\tan(\alpha)*o)] = 1 + (o/\cos(\alpha))$$

$$[\sin(\alpha)*h] + [\sin(\alpha)*(\tan(\alpha)*o)] = 1 + (o/\cos(\alpha))$$

$$\sin(\alpha)*h = [1 + (o/\cos(\alpha))] - [\sin(\alpha)*(\tan(\alpha)*o)]$$

$$h = [[1 + (o/\cos(\alpha))] * [\sin(\alpha)*(\tan(\alpha)*o)]]/\sin(\alpha)$$

Focus height h can therefore be calculated from all the possible angles and an array of angles can be created for each possible h. In order to compensate for the error in calculation using the simplified formula, a table is stored in master module 110 having the angle derivations for various focus distances h. This table is used for any distance from the minimum focus distance to 200 cm (Table A: Calculation of h from angle and conversion to microsteps, and Table B: Displaying distance, angle, and microsteps). However, by minimizing the length L, the simplified formula discussed with reference to FIG. 2 results in very little error and can therefore be used in its place.

TABLE A

| angle | radians | H | Steps | Steps Rounded |
|---|---|---|---|---|
| 0.1 | 0.001745 | 22.63496994 | 12969 | 0.888889 | 1 |
| 0.2 | 0.003491 | 22.63487977 | 6484 | 1.777778 | 2 |
| 0.3 | 0.005236 | 22.63472948 | 4323 | 2.666667 | 3 |
| 0.4 | 0.006981 | 22.63451907 | 3242 | 3.555556 | 4 |
| 0.5 | 0.008727 | 22.63424855 | 2594 | 4.444444 | 4 |
| 0.6 | 0.010472 | 22.63391792 | 2161 | 5.333333 | 5 |
| 0.7 | 0.012217 | 22.63352717 | 1853 | 6.222222 | 6 |
| 0.8 | 0.013963 | 22.63307631 | 1621 | 7.111111 | 7 |
| 0.9 | 0.015708 | 22.63256534 | 1441 | 8 | 8 |
| 1 | 0.017453 | 22.63199426 | 1297 | 8.888889 | 9 |
| 1.1 | 0.019199 | 22.63136308 | 1179 | 9.777778 | 10 |
| 1.2 | 0.020944 | 22.63067179 | 1081 | 10.66667 | 11 |
| 1.3 | 0.022689 | 22.62992039 | 997 | 11.55556 | 12 |
| 1.4 | 0.024435 | 22.6291089 | 926 | 12.44444 | 12 |
| 1.5 | 0.02618 | 22.62823731 | 864 | 13.33333 | 13 |
| 1.6 | 0.027925 | 22.62730562 | 810 | 14.22222 | 14 |
| 1.7 | 0.029671 | 22.62631384 | 763 | 15.11111 | 15 |
| 1.8 | 0.031416 | 22.62526197 | 720 | 16 | 16 |
| 1.9 | 0.033161 | 22.62415001 | 682 | 16.88889 | 17 |
| 2 | 0.034907 | 22.62297797 | 648 | 17.77778 | 18 |

TABLE B

| Dist | Array loc | Angle | Steps |
|---|---|---|---|
| 50 | 245 | 24.5 | 218 |
| 51 | 240 | 24 | 213 |
| 52 | 236 | 23.6 | 210 |
| 53 | 232 | 23.2 | 206 |
| 54 | 228 | 22.8 | 203 |
| 55 | 224 | 22.4 | 199 |
| 56 | 221 | 22.1 | 196 |
| 57 | 217 | 21.7 | 193 |
| 58 | 214 | 21.4 | 190 |
| 59 | 211 | 21.1 | 188 |
| 60 | 207 | 20.7 | 184 |
| 61 | 204 | 20.4 | 181 |
| 62 | 201 | 20.1 | 179 |
| 63 | 198 | 19.8 | 176 |
| 64 | 195 | 19.5 | 173 |
| 65 | 192 | 19.2 | 171 |
| 66 | 190 | 19 | 169 |
| 67 | 187 | 18.7 | 166 |
| 68 | 185 | 18.5 | 164 |
| 69 | 182 | 18.2 | 162 |
| 70 | 180 | 18 | 160 |
| 71 | 177 | 17.7 | 157 |
| 72 | 175 | 17.5 | 156 |
| 73 | 173 | 17.3 | 154 |
| 74 | 170 | 17 | 151 |
| 75 | 168 | 16.8 | 149 |
| 76 | 166 | 16.6 | 148 |
| 77 | 164 | 16.4 | 146 |
| 78 | 162 | 16.2 | 144 |
| 79 | 160 | 16 | 142 |
| 80 | 158 | 15.8 | 140 |
| 81 | 156 | 15.6 | 139 |
| 82 | 155 | 15.5 | 138 |
| 83 | 153 | 15.3 | 136 |
| 84 | 151 | 15.1 | 134 |
| 85 | 149 | 14.9 | 132 |
| 86 | 148 | 14.8 | 132 |
| 87 | 146 | 14.6 | 130 |
| 88 | 145 | 14.5 | 129 |
| 89 | 143 | 14.3 | 127 |
| 90 | 141 | 14.1 | 125 |
| 91 | 140 | 14 | 124 |
| 92 | 139 | 13.9 | 124 |
| 93 | 137 | 13.7 | 122 |
| 94 | 136 | 13.6 | 121 |
| 95 | 134 | 13.4 | 119 |
| 96 | 133 | 13.3 | 118 |
| 97 | 132 | 13.2 | 117 |
| 98 | 130 | 13 | 116 |
| 99 | 129 | 12.9 | 115 |
| 100 | 128 | 12.8 | 114 |

All the data acquired by the master module 110, including the corrected pivot angle described above, the LED color, and LED spot size, are sent sequentially to each peripheral modules 120 via the I2C serial bus. The microcontroller 500 converts the required angle to step position by dividing the angle by 1.8 degrees per step and multiplying by 16 microsteps (ms), where angle-to-microsteps is as follows: 1 step=1.8°, 16 microsteps/step and ms=(θ/1.8)*16.

Figure 9:
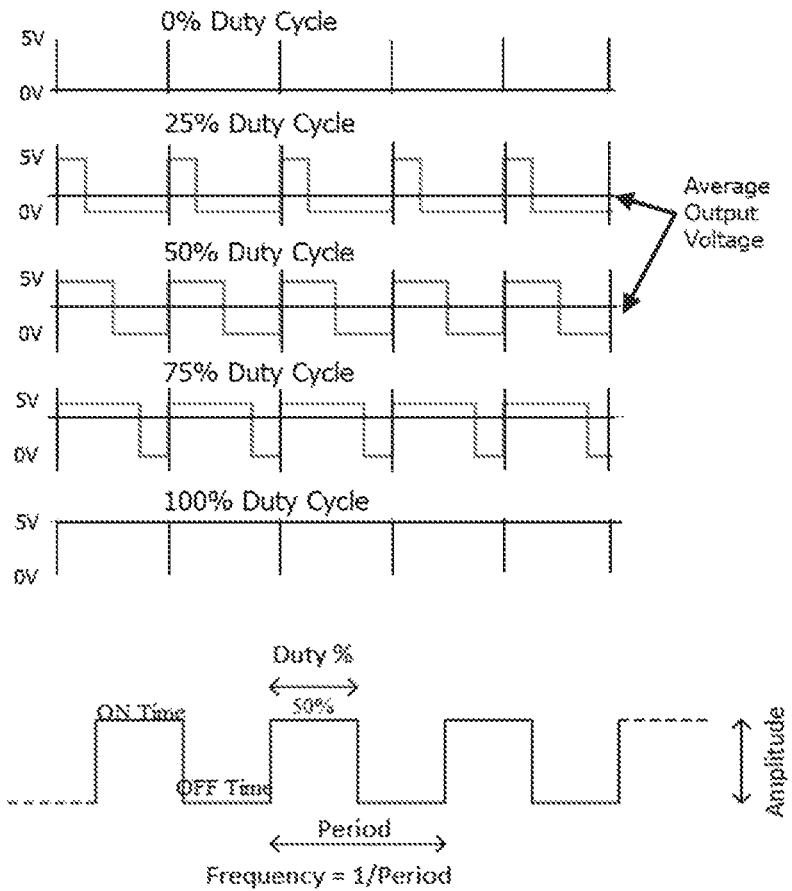
FIG. 9 shows pulse width modulated signals for controlling brightness of a lamp in an overhead lighting system, in accordance with an embodiment.

Brightness of the lamps 150 is controlled by varying the duty cycle of a PWM signal output from lamp driver 510, as shown in FIG. 9, which changes the overall output color of the lamps 150 because of their individual color temperatures. Lamp driver 510 can also shut down the outer LED row of lamp 150 if a smaller spot size is desired. Each LED color preferably comprises a pair of series connected LEDs. In order to shut down the outer row, a pair of MOSFETs (not shown) may be used to bypass the outer row of series connected LEDs.

In conclusion, an overhead lighting system is set forth for use, as an example to assist surgical operations, that is designed to enable a medical team to focus exclusively on a surgical operation. Current manual focusing OR lamps are imprecise, time consuming and can be frustrating for the surgical teams, leading to increased hospital costs, and potentially leading to surgical error compromising patient safety as well as to surgeon eye strain and fatigue. To mitigate these issues, the system set forth herein includes automatic focusing and variation of the lamp brightness, color temperature, and spot size. These features are applied seamlessly whenever the light is moved by the operating room staff and works with minimal user intervention.

The many features and advantages of the invention are apparent from the detailed specification. Further, since numerous modifications and changes will readily occur to those skilled in the art, it is not desired to limit the invention to the exact construction and operation illustrated and described, and accordingly all suitable modifications and equivalents may be resorted to. For example, although an embodiment of an overhead lighting system is set forth that facilitates positioning and automatically focuses light on a surgical operation site, it is contemplated that the features of the invention may advantageously be applied to other precision lighting applications, such as those used by architects, engineers, jewelers, to name but a few.

What is claimed is:

1. An overhead lighting system, comprising:
a master module having a sensor for measuring distance to an area of interest;
at least one peripheral module pivotally connected to the master module, the at least one peripheral module having at least one lamp and a mechanism for pivoting the at least one peripheral module to an angle relative to the master module based on the distance to the area of interest, for focusing the at least one lamp on the area of interest; and
wherein the master module further includes at least one of an accelerometer and gyroscope for detecting movement of the master module in three dimensions and activating the sensor to measure the distance to the area of interest and in response cause the at least one peripheral module to pivot to the angle for focusing the at least one lamp on the area of interest.

2. The overhead lighting system of claim 1, wherein the master module further includes a laser crosshair that is activated by the at least one of an accelerometer and gyroscope detecting movement of the master module, for illuminating the area of interest.

3. The overhead lighting system of claim 1, wherein the mechanism for pivoting the at least one peripheral module is a stepper motor or servo motor.

4. The overhead lighting system of claim 1, comprising a plurality of peripheral module pivotally connected to the master module by respective pivoting mechanisms all controlled by one of either a single motor or independent motors for each pivoting mechanism.

5. The overhead lighting system of claim 3, wherein the at least one peripheral module further includes either a proximity sensor or an absolute encoder to set an initial position of the stepper motor.

6. The overhead lighting system of claim 4, further including a proximity sensor or absolute encoder to set an initial position of the single motor or independent motors.

7. The overhead lighting system of claim 1, wherein the at least one lamp is an LED lamp and the at least one peripheral module further includes circuitry to control brightness, kelvin temperature color and spot size of the LED lamp.

8. The overhead lighting system of claim 7, wherein the circuitry to control brightness generates a drive signal for varying intensity of the at least one lamp according to modulated pulse width of the drive signal.

9. The overhead lighting system of claim 1, wherein the at least one lamp comprises at least one row of light emitting diodes (LEDs).

10. The overhead lighting system of claim 9, wherein the at least one row of light emitting diodes (LEDs) includes separate colored LEDs of different degrees Kelvin, respectively.

11. A method of operating an overhead lighting system having a master module, and at least one attached tiltable peripheral module having at least one lamp, the method comprising:
detecting motion of the master module;
illuminating an area of interest with a laser crosshair;
after the master module has stopped moving for a first time period then measuring distance to an area of interest;
calculating a pivot angle between the master module and the at least one peripheral module based on the measured distance;
repositioning the at least one peripheral module at the calculated pivot angle to focus the at least one lamp on the area of interest;
ceasing illumination of the area of interest with the laser crosshair.

12. The method of claim 11, wherein the area of interest is illuminated with the laser crosshair to pinpoint the area of interest during the first time period.

13. The method of claim 12, wherein ceasing illumination of the area of interest with the laser crosshair occurs after a second time period.

14. The method of claim 11, wherein the first time period is shorter than the second time period.

15. The method of claim 14, wherein the first time period is approximately 0.5 seconds and the second time period is approximately 10 seconds.

16. The method of claim 11, wherein measuring the distance to the area of interest comprises taking multiple distance measurements during the first time period and averaging the multiple distance measurements.

17. The method of claim 11, further comprising setting an initial position of the at least one peripheral module based on proximity of the at least one peripheral module to the master module.

18. The method of claim 11, further comprising controlling control brightness, kelvin temperature color and spot size of the at least one lamp.

19. The method of claim 11, where A is the measured distance, O is perpendicular to and is the distance from an edge of the master module to A and is , L is the width of the at least one peripheral module, and wherein O is opposite of an angle $\alpha = \tan^{-1}(O+L/A)$, and $\alpha = 180-(90+\beta)$, such that $\alpha = 90-\beta$ and $\theta = 90-\beta$, and $\alpha = \theta$ is the pivot angle necessary for the peripheral module to focus the at least one lamp on the area of interest.

* * * * *